(12) United States Patent
Dominici et al.

(10) Patent No.: US 9,572,838 B2
(45) Date of Patent: Feb. 21, 2017

(54) METHOD FOR PRODUCTION OF ANTI-TUMOR TRAIL PROTEIN

(71) Applicants: Massimo Dominici, Ferrara (IT); Rita Bussolari, Crevalcore (IT); Giulia Grisendi, Reggio Emilia (IT); Pierfranco Conte, Pisa (IT)

(72) Inventors: Massimo Dominici, Ferrara (IT); Rita Bussolari, Crevalcore (IT); Giulia Grisendi, Reggio Emilia (IT); Pierfranco Conte, Pisa (IT)

(*) Notice: Subject to any disclaimer, the term of this patent is extended or adjusted under 35 U.S.C. 154(b) by 0 days.

(21) Appl. No.: 14/657,993

(22) Filed: Mar. 13, 2015

(65) Prior Publication Data

US 2015/0320803 A1 Nov. 12, 2015

Related U.S. Application Data

(63) Continuation-in-part of application No. 13/266,767, filed as application No. PCT/IB2010/051850 on Apr. 28, 2010, now abandoned.

(30) Foreign Application Priority Data

Apr. 28, 2009 (IT) .................. MO2009A000100

(51) Int. Cl.
| | |
|---|---|
| *A61K 48/00* | (2006.01) |
| *C12N 15/86* | (2006.01) |
| *C07H 21/04* | (2006.01) |
| *A61K 35/35* | (2015.01) |
| *A61K 39/395* | (2006.01) |
| *A61K 38/19* | (2006.01) |
| *A01K 67/00* | (2006.01) |

(52) U.S. Cl.
CPC ............ *A61K 35/35* (2013.01); *A61K 38/191* (2013.01); *A61K 39/395* (2013.01); *A61K 39/39558* (2013.01)

(58) Field of Classification Search
CPC .................. A61K 35/35; A61K 39/39558
USPC ............ 424/93.21; 435/456, 320.1; 536/23.4
See application file for complete search history.

(56) References Cited

U.S. PATENT DOCUMENTS

| | | | | |
|---|---|---|---|---|
| 2002/0128438 | A1* | 9/2002 | Seol | C07K 14/70575 530/350 |
| 2007/0264239 | A1* | 11/2007 | Huard | C12N 5/0657 424/93.7 |
| 2011/0027239 | A1* | 2/2011 | Paek | A61K 35/28 424/93.21 |
| 2014/0086907 | A1* | 3/2014 | Shah | A61K 38/1774 424/133.1 |

OTHER PUBLICATIONS

Visvader et al. Cancer stem cells in solid tumours: accumulating evidence and unresolved questions. Nature Reviews 8:755-768, 2008.*
Sasportas et al. Assessment of thrapeutic efficacy and fate of engineered human mesenchymal stem cells for cancer therapy. PNAS 106:4822-4827, 2009.*
Zhang et al. pVAX1 plasmid vector-mediated gene transfer of soluble TRAIL suppresses human hepatocellular carcinoma growth in nude mice. Acta Biochimica Polonica 54:307-313, 2007.*

* cited by examiner

*Primary Examiner* — Quang Nguyen
(74) *Attorney, Agent, or Firm* — Themis Law; Franco A. Serafini; David M. Fortner

(57) ABSTRACT

A method for production of anti-tumor TRAIL includes inserting a TRAIL molecule, encoded by a viral vector irreversibly derived from a cell line, into a carrier cell, thereby obtaining a stably TRAIL-producing carrier cell, and wherein the TRAIL molecule includes a soluble molecule.

4 Claims, 13 Drawing Sheets

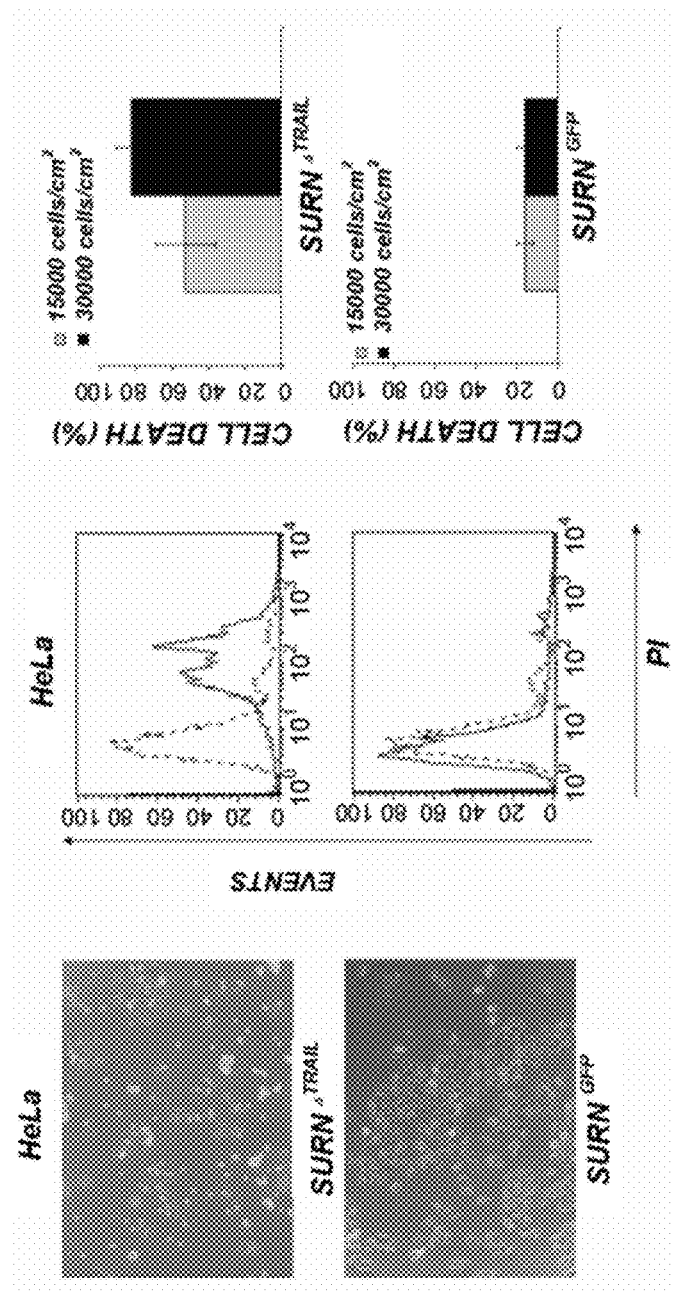

(STATE OF THE ART)

SEQUENCE LISTING

<160> NUMBER OF SEQ ID NOS: 6

<210> SEQ ID NO 1
<211> LENGTH: 35
<212> TYPE: DNA
<213> ORGANISM: Unknown
<220> FEATURE:
<223> OTHER INFORMATION: TRAIL

<400> SEQUENCE: 1
cagatctggt gagagaaaga ggtcctcaga gagta      35

```
<210> SEQ ID NO 2
<211> LENGTH: 29
<212> TYPE: DNA
<213> ORGANISM: Unknown
<220> FEATURE:
<223> OTHER INFORMATION: TRAIL

<400> SEQUENCE: 2
ggaattcctt agccaactaa aaaggcccc                                     29

<210> SEQ ID NO 3
<211> LENGTH: 20
<212> TYPE: DNA
<213> ORGANISM: Unknown
<220> FEATURE:
<223> OTHER INFORMATION: TRAIL

<400> SEQUENCE: 3
gtaaacggcc acaagttcag                                               20

<210> SEQ ID NO 4
<211> LENGTH: 20
<212> TYPE: DNA
<213> ORGANISM: Unknown
<220> FEATURE:
<223> OTHER INFORMATION: TRAIL

<400> SEQUENCE: 4
tgtcggccat gatatagacg                                               20

<210> SEQ ID NO 5
<211> LENGTH: 20
<212> TYPE: DNA
<213> ORGANISM: Unknown
<220> FEATURE:
<223> OTHER INFORMATION: TRAIL

<400> SEQUENCE: 5
gcagtggcaa agtggagatt                                               20

<210> SEQ ID NO 6
<211> LENGTH: 20
<212> TYPE: DNA
<213> ORGANISM: Unknown
<220> FEATURE:
<223> OTHER INFORMATION: TRAIL

<400> SEQUENCE: 6
gcagaagggg cggagatgat                                               20
```

METHOD FOR PRODUCTION OF ANTI-TUMOR TRAIL PROTEIN

CROSS-REFERENCE TO RELATED APPLICATIONS

The present application is a continuation-in-part of application Ser. No. 13/266,767 having a filing date of Oct. 27, 2011, which is the national stage of international application no. PCT/IB2010/051850 having a filing date of Apr. 28, 2010, which claims priority to Italian application no. MO2009A000100 having a filing date of Apr. 28, 2009, all of which are incorporated herein by reference in their entireties.

INCORPORATION BY REFERENCE OF MATERIAL SUBMITTED AS TEXT FILE VIA THE OFFICE ELECTRONIC FILING SYSTEM (EFS-WEB)

The material submitted as a text file named SLi20120111_ST25_1 created on Mar. 6, 2015 and having a size of 1263 bytes is incorporated herein by reference.

FIELD OF THE INVENTION

The present invention relates to a method for production of anti-tumor TRAIL, which can be carried out ex vivo, i.e. outside the patient's body, by genetic modification of carrier cells.

BACKGROUND OF THE INVENTION

The word TRAIL is known to technically define a molecule belonging to the family of the so-called "death ligands", i.e. a family of Tumor Necrosis Factor molecules (TNF), In practice, a TRAIL molecule can induce cell death in diseased tissues only, and spare healthy tissues, and for this characteristic it is a particularly interesting molecule for use in oncological treatments and in other biomedical fields.

TRAIL-based treatment of an organism affected by tumor cells may occur in two particular manners: in the former, the TRAIL molecule is chemically synthesized beforehand, in which case it is defined as recombinant TRAIL, and later administered to the tumor-affected organism; in the latter the TRAIL molecule may be introduced into a tumor-affected organism through a carrier consisting of a TRAIL-producing cell.

In the former case, the need was found for combined use of chemotherapeutic agents to enhance anti-tumor effects, because the latter have been found to progressively decrease, due to the very short half-life of the TRAIL molecule, i.e. of the order of 20/30 minutes, the high renal excretion rate of this molecule, and TRAIL resistance. The combination with chemotherapeutic drugs encourages the use of the recombinant TRAIL molecule due to its specific tumor cell eliminating capacity, but this combination is affected by high toxicity toward hepatocytes, lymphocytes and osteoblasts, and leads to undesired side effects for the organism.

Furthermore, due to short half-life and high excretion rate, repeated administration of chemotherapeutic drugs was required in combination with TRAIL and this caused a considerable increase of overall costs upon repeated TRAIL administrations. In the latter case, the TRAIL molecule is contained in a virus that is used as a vector therefor and allows release of its genetic makeup containing the TRAIL-encoding sequence, which is later translated into a protein and transferred to the membrane of the cell infected by such viral vector.

These infected cells become the medium that carries TRAIL in direct contact with target tumor cells, thereby causing apoptosis thereof.

The viral vectors used heretofore are vectors that belong to the lentivirus or adenovirus family.

The cells infected by these vectors can carry the TRAIL molecule to the location of the organism in which an anti-tumor effect, i.e. apoptosis of neoplastic cells is required.

For this purpose, multiple cell types are used, which all have a particular tropism for tumor disease sites: for example, hematopoietic stem cells and mesenchymal stem cells are used.

Nevertheless, this prior art still has certain drawbacks.

A first drawback is that the viral vector in use may have considerable restrictions of use due to its biological properties.

For instance, if an adenovirus is used, the greatest restriction consists in the inability of the viral genome to be stably integrated in the genome of infected cells, and this characteristic generates a transient, short-lasting form of TRAIL, which is designed to deplete, thereby causing a limitation of the duration of the therapeutic effect, like in the infusion of recombinant TRAIL.

An additional drawback, independent of the viral vector in use, is that the studies that have been conducted and published heretofore have concerned application of TRAIL only as a transmembrane protein and disregarded the existence of a biologically active domain of the molecule even in the form of a soluble ligand having a strong anti-tumor activity. This involved the generation of cell vectors that could only produce TRAIL cells as membrane proteins capable of inducing selective apoptosis of the target tumor cell only through direct contact allowed by interaction between the TRAIL on the carrier cell and its receptor on the target tumor cell; therefore, the membrane TRAIL carrying cell must be necessarily located in the proximity of or in contact with the tumor mass to ensure its therapeutic effect.

Another drawback is that the membrane TRAIL-carrying cell located in the tumor mass must survive and proliferate for the time required to exert its anti-tumor action; thus, the cell dose to be infused must be substantially comparable to the number of tumor cells to be eliminated, because cytotoxic action only occurs through cell contact.

As mentioned above, this causes high cell production costs and may give rise to side effects associated to infusion in the patient.

Another drawback is that the lack of an excreted TRAIL form has prevented more intensive pharmacokinetic studies on infused cells, and the duration of its effect with time could not be understood.

A further drawback is that carrier cells such as bone-marrow derived cells, have been used in the studies, without considering that these might produce molecules that can inhibit or even block the anti-tumor action of TRAIL molecules. The cell used as a carrier shall produce a small number of or no decoy receptors (such as OPGs), i.e. receptors capable of sequestering Finally, the cell that is used as a carrier, in the case of stem cells, shall not have the TRAIL-specific receptors (DR4 and DR5) potentially capable of causing the suicide of the carrier cell, and hence hindering any therapeutic effect.

Recent studies have suggested that a tumor is a complex mixture composed by different cell types with different grade of malignancy (Mueller M M and Fusenig N E, Nature Reviews 2004). In several malignancies it has been identified a small population of tumor cells sharing many similarities with normal stem cells including self-renewal and multipotency, and for this reason defined cancer stem cells (CSC) (Visvader J E and Lindeman G J, Nature Reviews 2008).

CSC have the ability to regenerate a new CSC and to give rise to the variety of proliferating and differentiated cancer cells that make up of the bulk of a tumor (Al-Hajj M and Clarke M F, Oncogene 2004).

Inside the tumor CSC reside in a well-described compartment defined "CSC niche".

The niche microenvironment regulates CSC stemness and proliferation influencing tumor progression and metastasis formation. In addition, it plays a protective role shielding them from environmental insults (Borovski T et al. Cancer Res, 2011).

Thanks to this defensive microenvironment in which CSC reside and due to specific cellular mechanisms that they develop including relative quiescence, high expression of several ABC drug transporters, active DNA-repair capacity and a resistance to apoptosis, CSC display an effective drug-resistance that allows them to survive to the chemotherapy treatment, repopulating the tumour and provoking disease relapse (Dean M et al. Nature Reviews 2005).

For this reason, CSC eradication represents the target for enduring curative effects after treatments. Unfortunately, these cells are resistant to the majority of the conventional therapies, therefore they have been very difficult to eliminate (Yi S Y and Hao Y B Cancer Treatment Reviews 2013).

In addition, due to their low frequency in tumor burden, the identification of CSC sub-population is not easy achievable. Many different markers have been used to characterize these cells. Among these, CD133 represents one of the most common used antigens for CSC identification and isolation (Grosse-Gehling P et al. J Pathol. 2013).

In addition, due to their stem-like properties these cells show high levels of stem-related genes such as OCT4, NANOG, SOX2 and c-Myc (Cabarcas S M et al. International Journal of Cancer 2011; Heddleston J M et al. Br J Cancer 2010). In particular, c-Myc is a well-known important regulator in the G1/S phase transition and self-renewal in stem cells and it has been extensively studied for its instrumental role in proliferation and growth of neoplastic cells (Shachaf C M and Felsher D W Cancer Res 2005). More, c-Myc has been recently recognized as an important regulator of stem cell biology connecting malignancy and "stemness".

In CSC, c-Myc activates an embryonic stem cell-like transcriptional module, which strongly correlates with tumor metastasis, proliferation and maintenance (Jialiang Wang, et al. PlosOne 2008; Sheelu Varghese et al. PlosOne 2012; Robyn T. Sussman et al. Cancer Biology & Therapy 2007).

In these years in vitro and in vivo studies by applicants have demonstrated that the pro-apoptotic molecule TRAIL delivered by human pericytes extracted from adipose tissue (AD-PC) is particularly active to induce tumor cell apoptosis in several different epithelial and mesenchymal cancer types including cervical carcinoma, pancreas, colon, multiple myeloma, osteosarcoma, rhabdomyosarcoma and Ewing's sarcoma.

Interestingly, the anticancer effect displayed by TRAIL when delivered by AD-PC in some cases resulted even more effective than the one obtained with the recombinant protein (Grisendi G. et al Cancer Res 2010; Grisendi G. et al Stem Cells 2014).

The action of TRAIL is related to its interaction with functional TRAIL receptors (DR4 and DR5) that are widely expressed on cancer cells surface. Ligand and receptor binding trigger the apoptotic signal inside the target cell. This signal induces the activation of two apoptotic pathways, defined one as extrinsic and the other as intrinsic.

The extrinsic pathway is activated when TRAIL binds to DR4 and/or DR5, inducing receptor oligomerization and the recruitment of Fas-associated protein with death domain (FADD) on the intracellular side. This complex contributes to the formation of the DISC when inactive pro-caspase 8 is recruited.

Auto-activation of the DISC may promote the activation of caspase-8 causing the cleavage and subsequent activation of the effector caspases-3, -6, -7 leading to the execution of apoptosis. In addition to DNA fragmentation and membrane bebbling, the activated caspase-8 may promote the cleavage of a pro-apoptotic Bcl-2 family member called Bid.

Bid represents the connection with the intrinsic apoptotic pathway, whose activation concomitant with the extrinsic pathway may be necessary for an efficient apoptosis in certain cell types. Bid on turn interacts with Bax/Bak causing the release of the cytocrome c from mitochondria.

This contributes to the formation of the apoptosome with APAF-1 and pro-caspase-9 that gets activated the effector caspases, leading to the hallmarks of apoptosis (Johnstone R W et al. Nature Reviews 2008; Holoch P A European Journal of Pharmacology 2009).

It is known that c-Myc oncoprotein represents one of the major catalysts of TRAIL sensitivity and its overexpression dramatically sensitizes cells to the apoptotic action of TRAIL. One of the mechanisms by which c-Myc enforce TRAIL apoptotic signal is represented by up-regulation of DR4 and DR5 receptors (Sussman R T Cancer Biology & Therapy 2015; Wang Y et al. Cancer Cell 2004). Moreover c-Myc augments TRAIL-dependent activation of caspase-8 through transcriptional inhibition of FLIP, which antagonizes generation of active caspase-8 in DISC (Ricci M S et al. Molecular and Cellular Biology 2004).

Finally, it was shown that c-Myc controls a "feedback amplification loop" involving activation of Bak and amplifies the TRAIL-induced caspase-8-Bid signals to induce full-blown apoptosis (Nieminen A I et al. Cell Cycle 2007).

SUMMARY OF THE INVENTION

It is a technical purpose of the invention to improve the prior art.

One object of the invention is to provide a method for producing anti-tumor TRAIL that allows the generation of a cell population whose phenotype can be associated with human pericytes extracted from adipose tissue (AD-PC).

Another object of the invention is to allow the cell population that can be associated with human pericytes to produce a soluble TRAIL form, to obtain an anti-tumor action that is not only localized, i.e. limited to the areas that can be reached by the pericytes, but also systemic, due to the release of TRAIL into circulation.

Another object of the invention is to provide a method for production of anti-tumor TRAIL, that reduces simultaneous administration of TRAIL-enhancing chemotherapeutic drugs, thereby limiting undesired side effects for the organism and allowing substantial cost-effective TRAIL administration.

In one aspect, the invention provides a method for production of anti-tumor TRAIL, which comprises: inserting a TRAIL molecule, encoded by a viral vector into a carrier cell, thereby obtaining a stably TRAIL-producing carrier cell, characterized in that said TRAIL molecule is of soluble type.

In another aspect, the invention provides a method for efficient, constant and stable production of a viral vector, encoding soluble TRAIL by stable producing lines derived from tumor cells.

In another aspect, the invention relates to an anti-tumor cell, comprising: a nucleus and a cytoplasm, a permanently modifying agent, characterized in that said infecting agent comprises a TRAIL molecule encoded by a viral vector and introduced into said nucleus of said cell.

Therefore, the method for production of anti-tumor TRAIL and the anti-tumor cell includes the steps of:

providing a cell population having a phenotype that can be associated with human pericytes;

allowing the cell population that can be associated with human pericytes to produce a soluble TRAIL form, to obtain an anti-tumor action that is not only localized, i.e. limited to the areas that can be reached by the pericytes, but also systemic, due to the release of TRAIL into circulation;

reducing simultaneous administration of TRAIL-S enhancing chemotherapeutic drugs, thereby eliminating undesired side effects for the organism and affording substantially cost-effective TRAIL administration.

During further studies performed to validate the approach to deliver TRAIL by adipose pericytic cells (AD-PC), it has been unexpectedly revealed new anti-cancer properties described in detail hereinafter. This is indicative of a c-Myc up-regulation that could be associated with an increased TRAIL sensitivity.

BRIEF DESCRIPTION OF THE DRAWINGS

Further features and advantages of the invention will be more readily apparent upon reading of the description of one embodiment of a method for production of anti-tumor TRAIL, which is shown hereinafter as a non limiting example, and in which:

FIG. 1 is a schematic representation of various functional domains of the TRAIL construct, in which:

Figure 2:
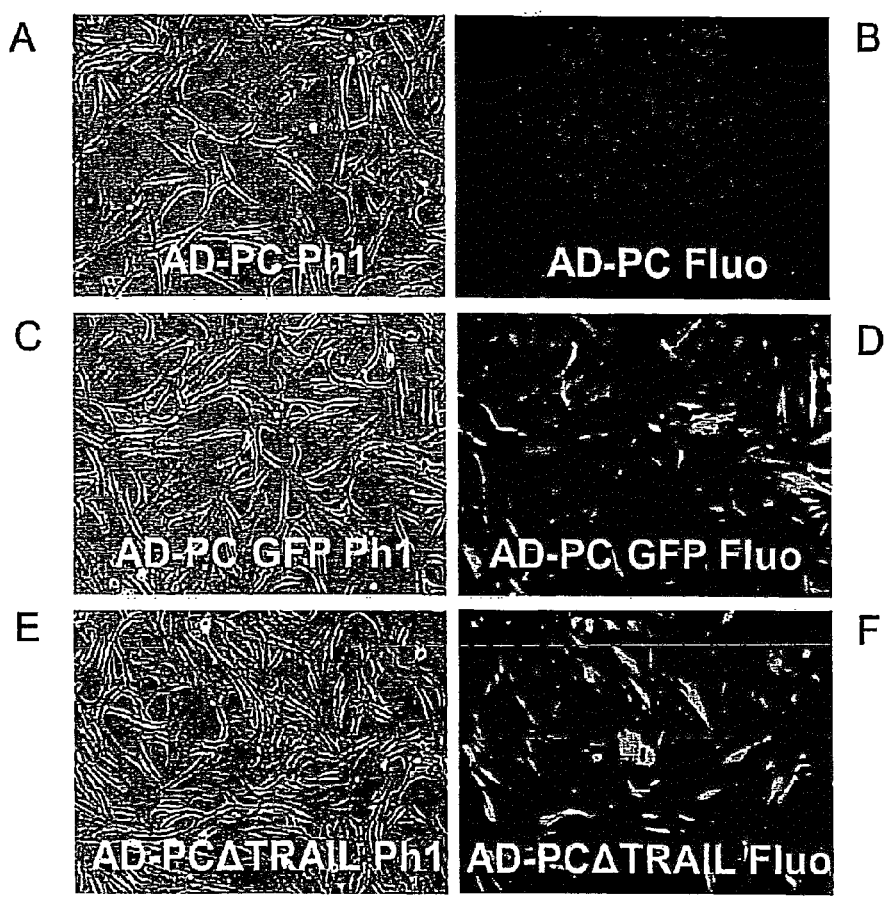
Figure 3:
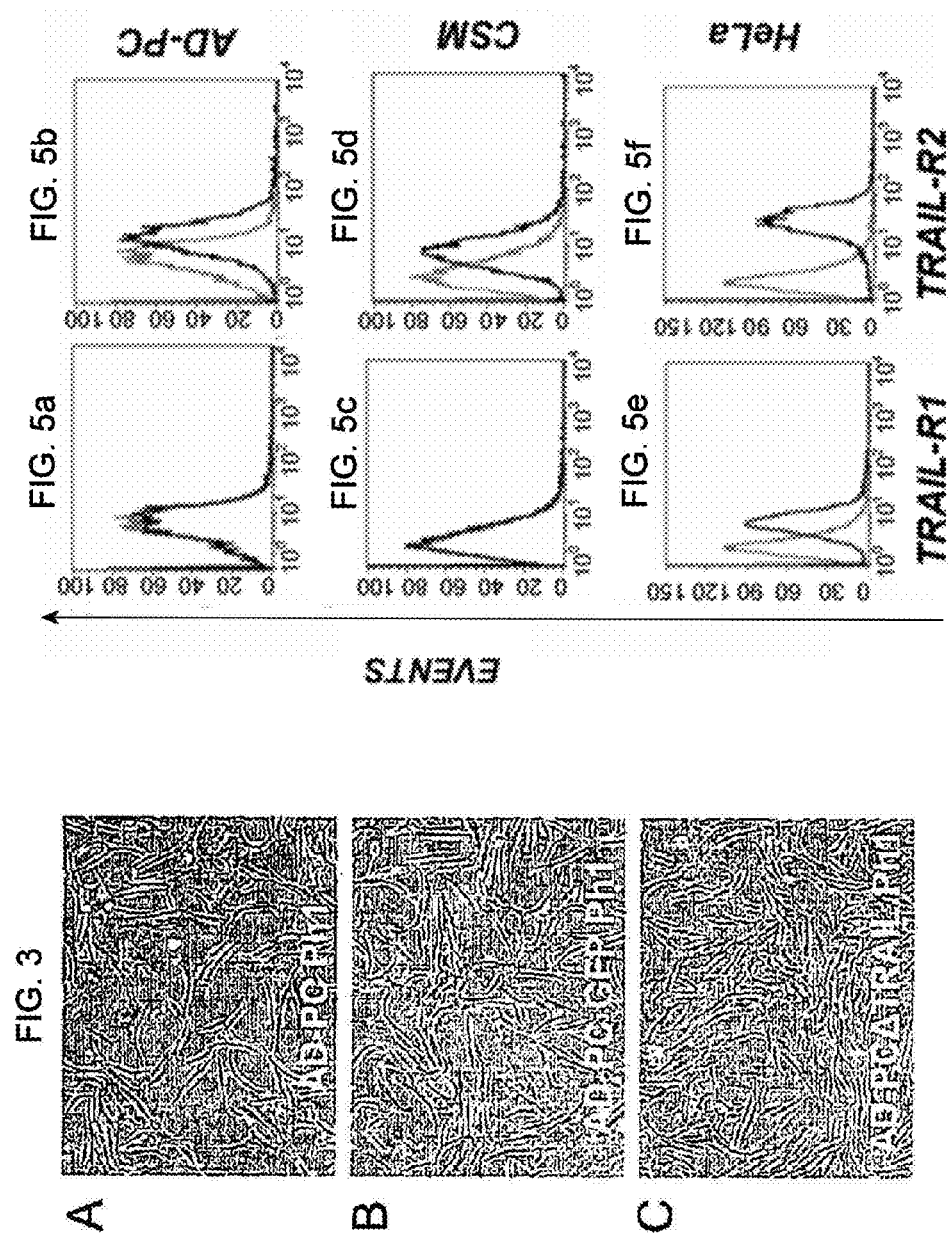
Figure 4:
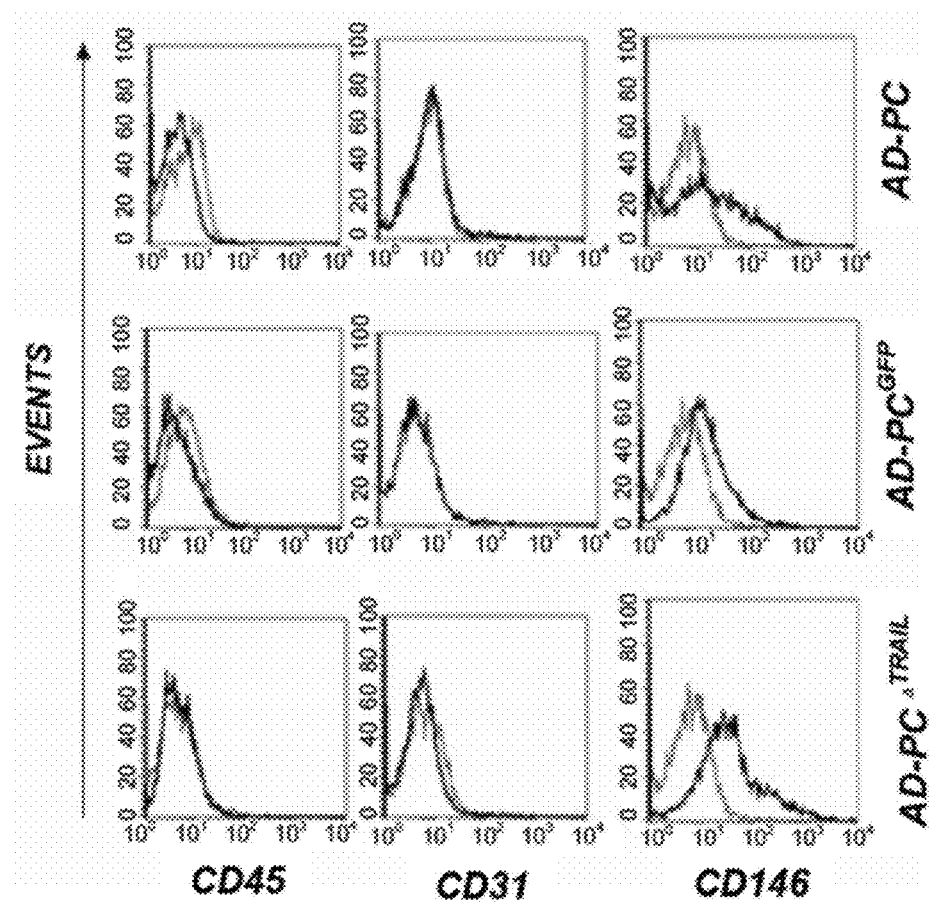
Figure 6:
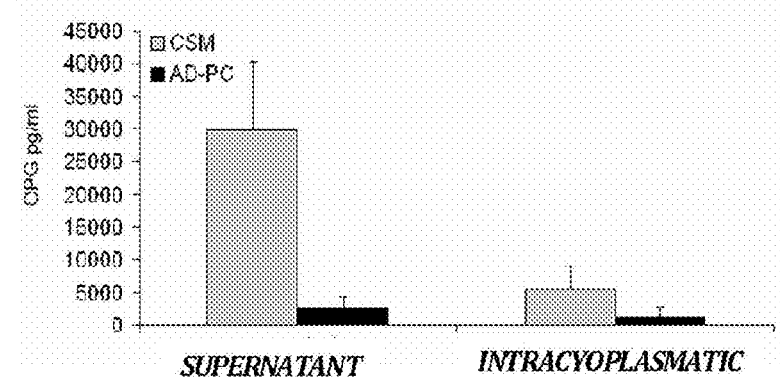
Figure 7:
Figure 8:
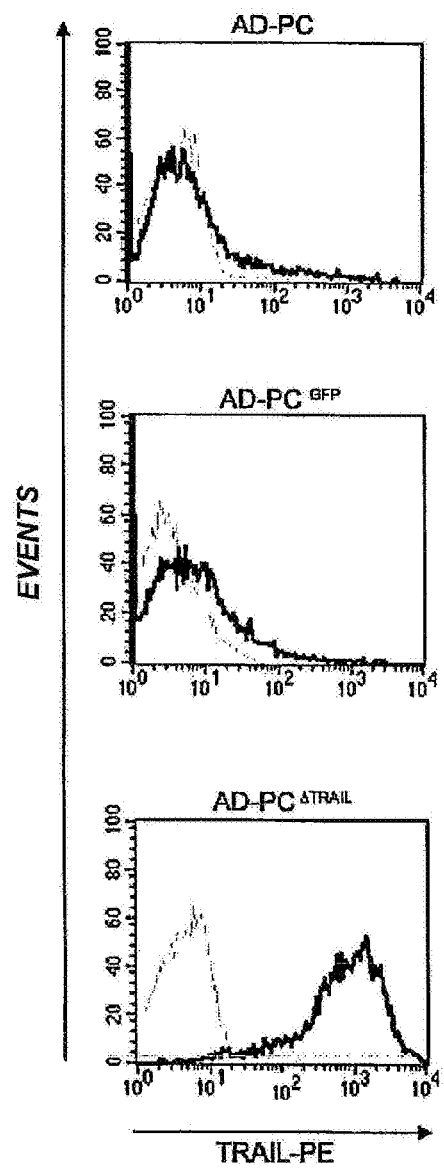
Figure 9:
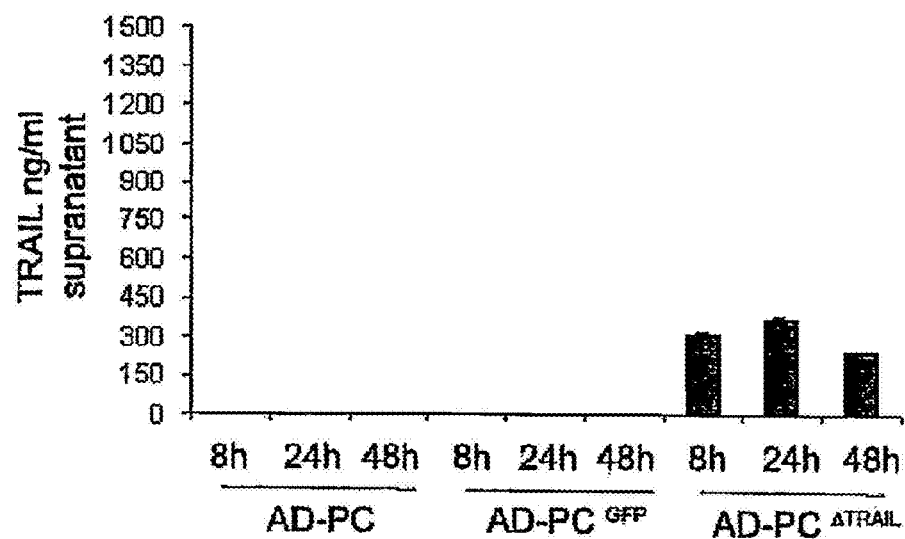
Figure 10:
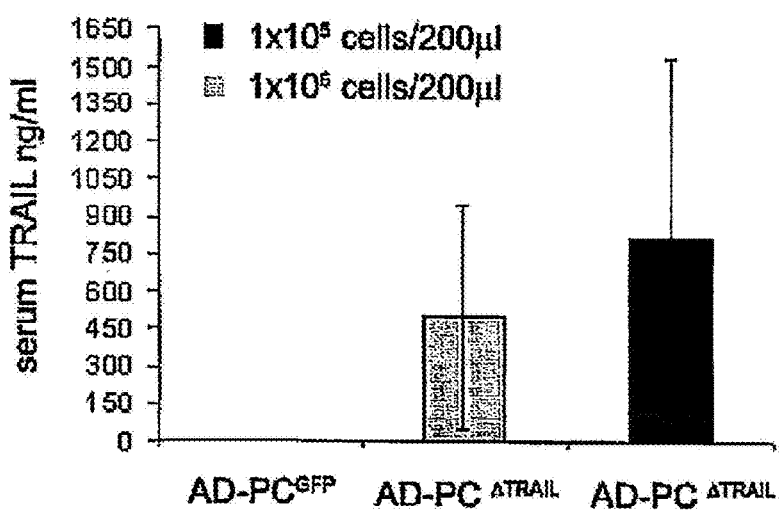
Figure 12A:
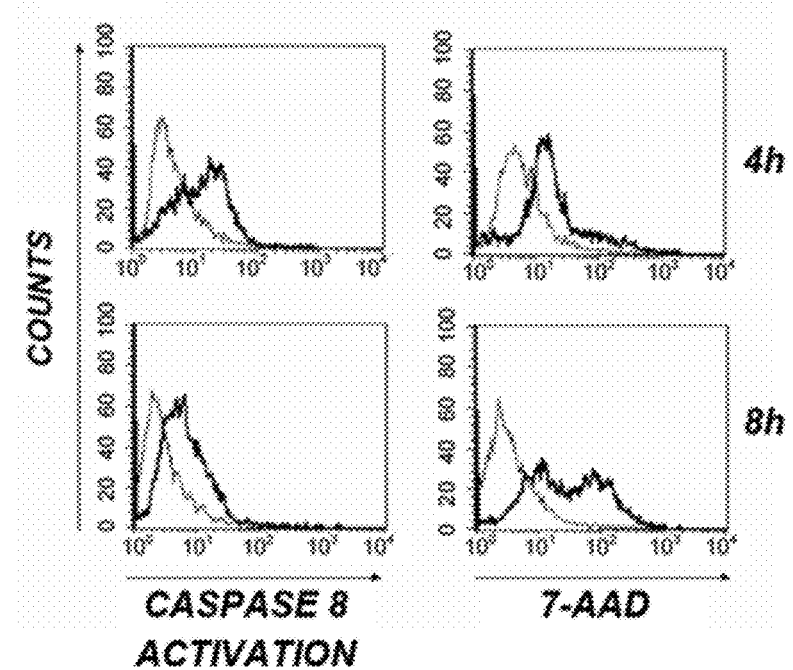
Figure 13:
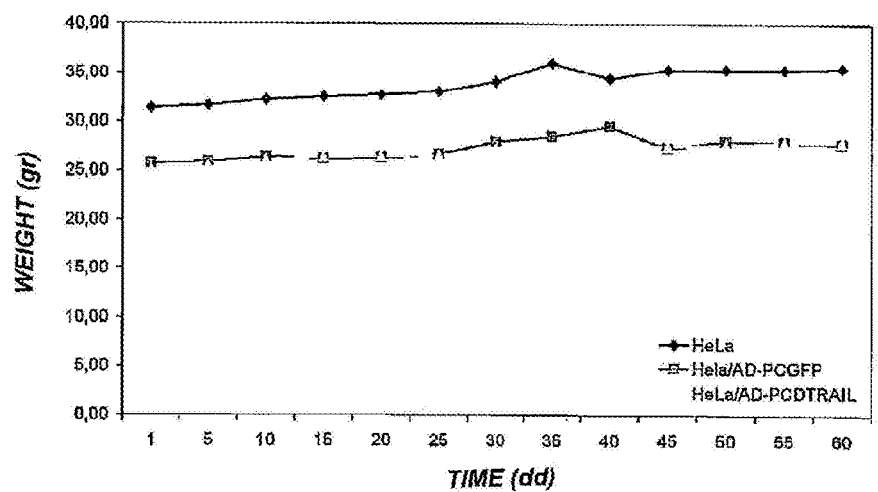
Figure 14:
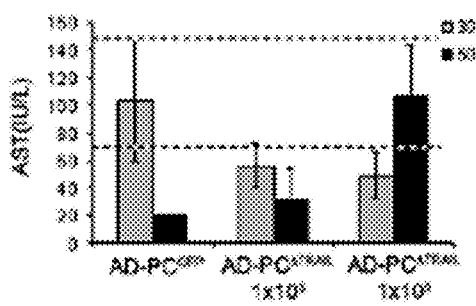
Figure 15:
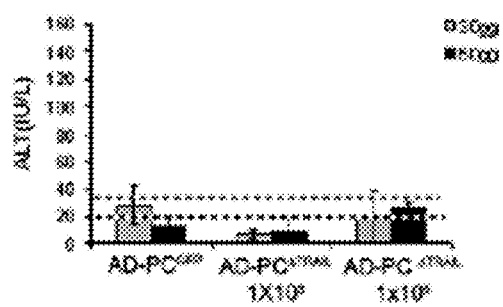
Figure 16:
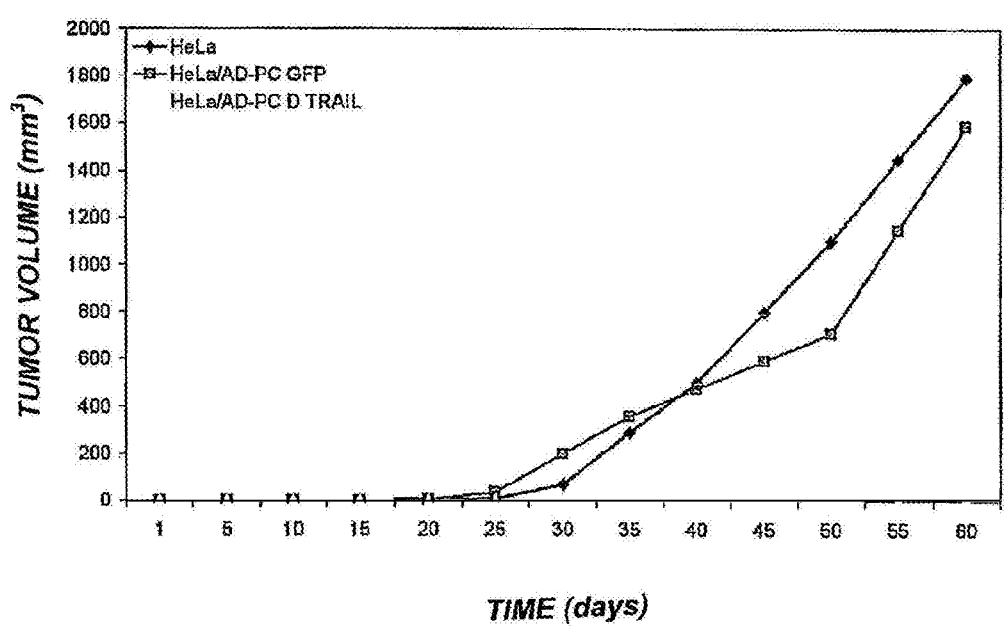
Figure 17:
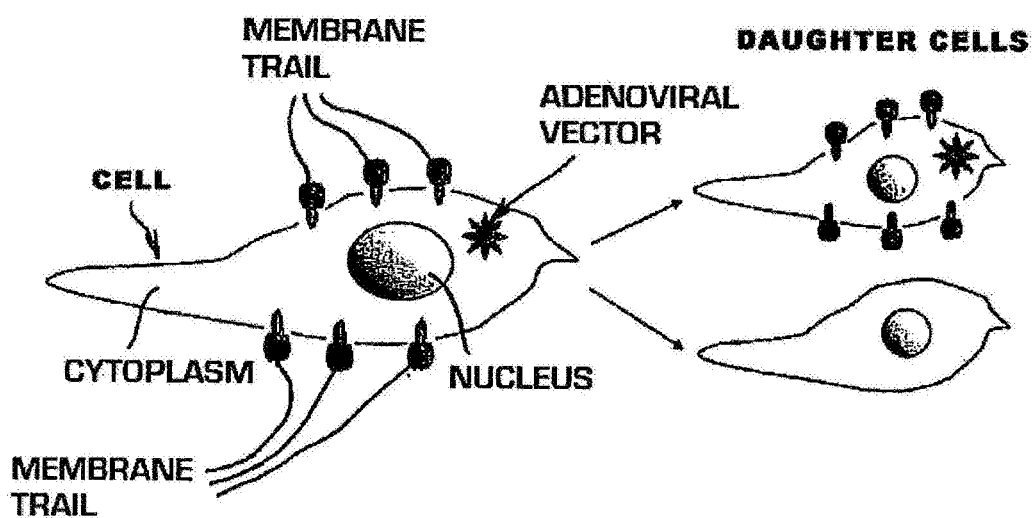
Figure 18:
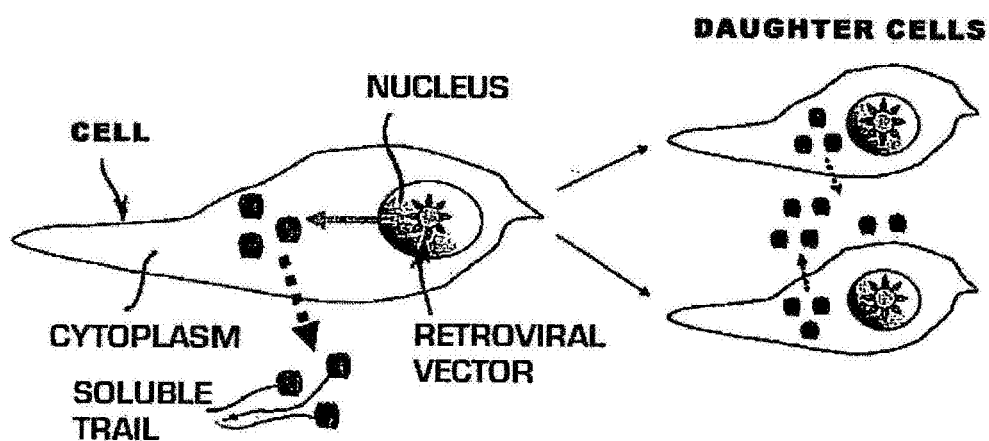
Figure 19:
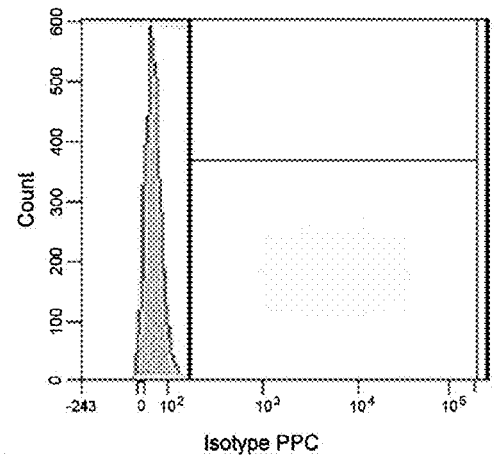
Figure 20:
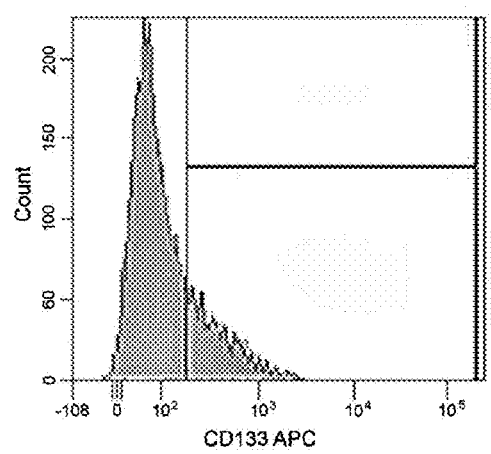
Figure 21:
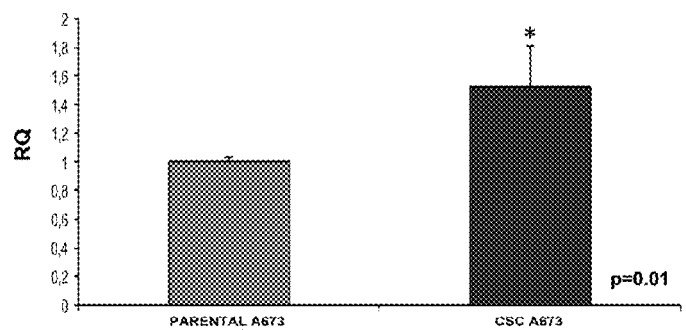
Figure 22:
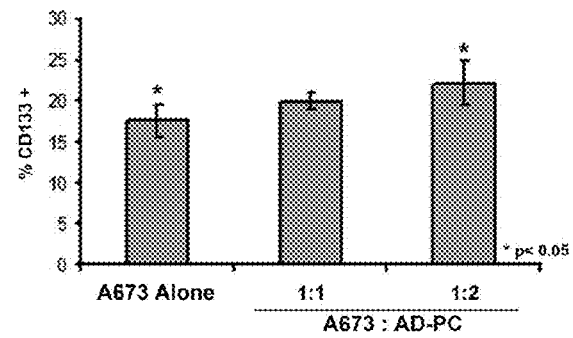
Figure 23:
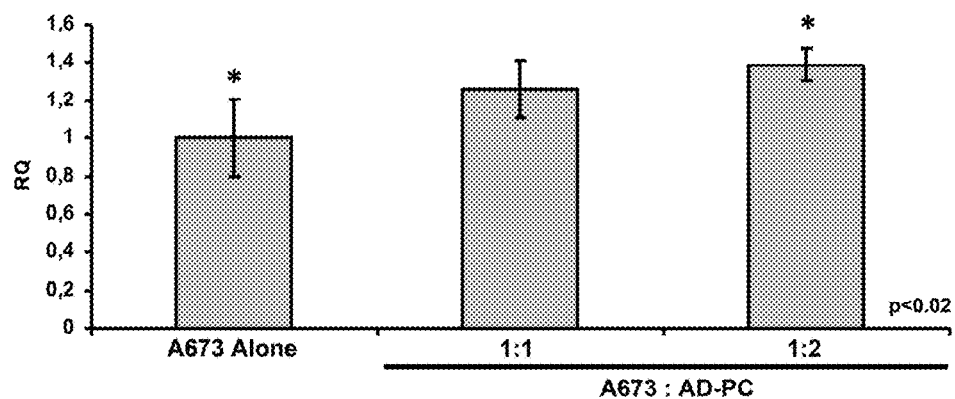
Figure 24:
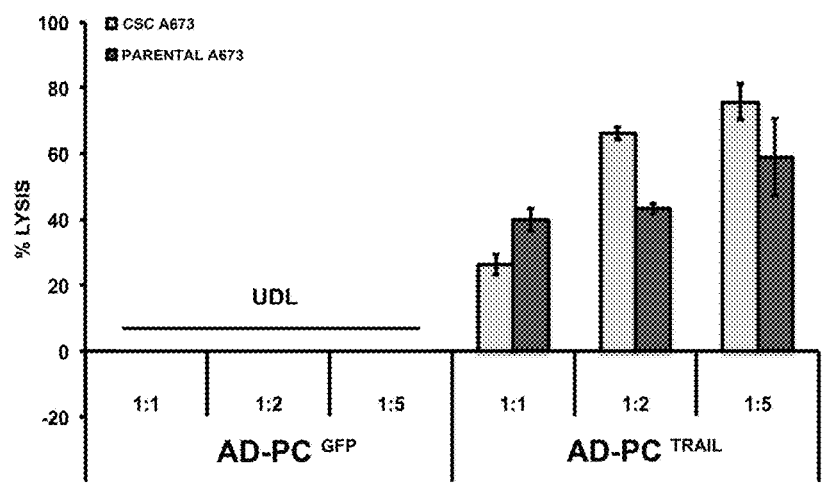
Figure 25:
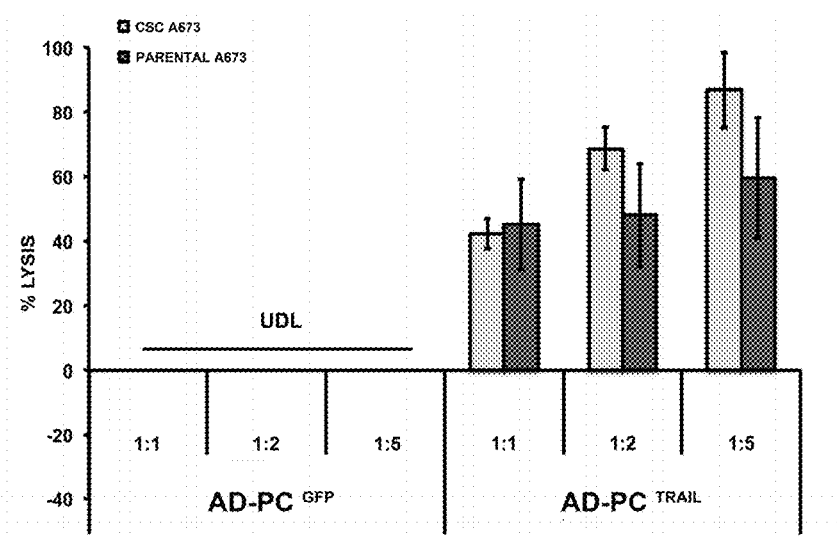

SS is a secretion signal or signal peptide;

F-CV (Furin-specific cleavage site) is a specific cleavage site for removal of the signal peptide by proteolytic cleavage after protein synthesis;

ILZ (Isoleucine zipper) is a trimerization domain;

hTRAILcDNA is a sequence corresponding to human TRAIL from aa 114 to 281;

FIG. 2 from A to F are reverse fluorescence microscope images (×10 magnification) which show an optimal infection process given by the typically green color of the cells infected by a GFP-expressing viral vector (presence of the GFP protein) and in which:

A, B) cultured AD-PC with and without fluorescence respectively;

C, D) AD-PC GFP genetically modified by a retroviral vector encoding the GFP protein, with and without fluorescence respectively;

E, F) AD-PC ΔTRAIL with and without fluorescence respectively;

FIG. 3 shows a phenotypic aspect of cultured AD-PC, AD-PC$^{GFP}$ e AD-PC$^{\Delta TRAIL}$, showing that handling of these cells with retroviral vectors (3B, C) does not change their aspect (×10 magnification);

FIG. 4 shows an immunophenotype, i.e. a cytofluorimetric analysis, which shows how the retroviral infection did not alter the expression of AD-PC-characteristic phenotypic markers (CD45$^-$, CD31$^-$, CD146$^+$);

FIGS. 5a to 5f show an expression of TRAIL receptors by cytofluorimetric analysis to define the receptor status (TRAIL-R1, TRAIL-R2) of TRAIL on AD-PC and on HeLa cells; particularly, FIG. 5a shows the expression of TRAIL-R1 on AD-PC in a genetically unmodified condition; FIG. 5b shows the expression of TRAIL-R2 on AD-PC in a genetically unmodified condition; FIGS. 5c and 5d show the corresponding expressions of FIGS. 5a and 5b in a TRAIL-producing genetically modified condition; FIGS. 5e and 5f show the expressions of TRAIL R1 and R2 respectively, on HeLa tumor cells;

FIG. 6 shows the an ELISA assay of OPG released in the supernatant of AD-PC and MSC (mesenchymal stem cells) from bone marrow, which shows that the OPG levels produced by AD-PC are much lower than the OPG levels released by bone marrow MSC;

FIG. 7 is Western Blot of ΔTRAIL protein expression with columns 1 and 2 showing that the antibody has highlighted a band of about 21 kDa corresponding to the ΔTRAIL protein in the protein lysate and in the supernatant of AD-PC ΔTRAIL whereas no band was detected at the AD-PC GFP protein lysate;

FIG. 8 shows the result of a cytofluorimetric analysis on the expression of ΔTRAIL protein;

FIG. 9 shows a quantitative ELISA assay of ΔTRAIL protein in AD-PC, AD-PC GFP and AD-PC ΔTRAIL supernatants: TRAIL values of 200-400 ng/ml are detected in AD-PC ΔTRAIL;

FIG. 10 shows a quantitative ELISA assay of A TRAIL protein in sera of animals with AD-PC GFP and AD-PC ΔTRAIL $1\times10^5$ and $1\times10^6$: TRAIL values of 500-750 ng/ml are detected in AD-PC ΔTRAIL;

FIG. 11 shows that AD-PC ΔTRAIL induces cell death in HeLa cells. The reversed microscope image (A) shows the presence of apoptotic bodies after 24 hours growth of HeLa cells in the supernatant of AD-PC$^{\Delta TRAIL}$ (×10 magnification). The cytofluorimetric analysis (B) shows a peak of cells displaced to high fluorescence values (Figure B higher) corresponding to an apoptotic event of HeLa in contact with the supernatant of AD-PC$^{\Delta TRAIL}$. No event was detected in HeLa cells in contact with the supernatant of AD-PC$^{GFP}$;

FIG. 12 shows caspase-8 activation. Culturing of HeLa cells with the supernatant of AD-PC$^{\Delta TRAIL}$ induces caspase-8 activation in the tumor line. The figure shows that, after 8 hours contact with the supernatant of AD-PC$^{\Delta TRAIL}$, 40% of HeLa cells has caspase-8 activation (early apoptosis) and 50% is positive to 7-AAD, which identifies necrotic cells. Using a caspase-8 inhibitor, Z-VAD-FMK, the apoptotic process is stopped;

FIG. 13 shows the weight of animals monitored during a 60 day treatment;

FIGS. 14 and 15 show an assay of murine hepatic enzymes: no appreciable changes in AST and ALT concentrations have been found during a 60 days treatment;

FIG. 16 shows the formation of a tumor mass monitored upon inoculation of AD-PC$^{GFP}$ and AD-PC$^{\Delta TRAIL}$. Control groups are found to show the appearance of a tumor mass after 20 days, unlike animals AD-PC$^{\Delta TRAIL}$-inoculated animals, in which tumor growth is strongly inhibited;

FIG. 17 is a schematic representation of a cell division phase for an anti-tumor cell with a prior art adenovirus inserted therein;

FIG. 18 is a schematic representation of a cell division phase for an anti-tumor cell with a retrovirus of the invention inserted therein;

FIG. 19 is a diagram view of flow cytometry data showing an isotype control staining for the analysis related to the expression of surface antigen CD133, as hallmark of sarcoma CSC. The light grey curve represents a negative signal. In the y-axis the number of cells considered, while on the x-axis the staining intensity;

FIG. 20 is a diagram view of flow cytometry data showing a staining for the analysis related to the expression of the antigen CD133 as hallmark of sarcoma CSC. The shift of the grey curve toward the right (x axis) suggests the expression of CD133 in the overall population of the considered sarcoma cell line A673. In the y-axis the number of cells considered, while on the x-axis the staining intensity;

FIG. 21 is a diagram view of c-myc expression (y axis) by real-time PCR in the overall considered sarcoma population of A673 (grey bar) compared with the selected fraction of sarcoma CSC (dark bar);

FIG. 22 is a diagram view of CSC levels (y axis) in the overall population of considered sarcoma cell line A673 (A673 alone) versus the CSC levels of A673 co-cultured with AD-PC at the same ratio (1:1) or with 2 fold of A673 with AD-PC (1:2). The statistics (by two tailed t-test) is significant starting from 1:2 ratio;

FIG. 23 is a diagram view of the c-myc expression by real-time PCR in the overall considered sarcoma population of A673 alone versus c-myc expression in A673 co-cultured with AD-PC at the same ratio (1:1) or with 2 fold of A673 with AD-PC (1:2). The statistics (by two tailed t-test) is significant starting from 1:2 ratio;

FIG. 24 is a diagram view of cytotoxicity assays due to TRAIL measuring deathly-lysed cells (in the y axis) in both the overall sarcoma cell population (parental A673 in black bars) and in the selected CSC (in grey bars). The comparison regards AD-PC not expressing TRAIL (GFP) and AD-PC expressing TRAIL at different ratios between A673 and AD-PC (1:1; 1:2; 1:5) at 8 hours of co-culture;

FIG. 25 is a diagram view of cytotoxicity assays due to TRAIL measuring deathly-lysed cells (in the y axis) in both the overall sarcoma cell population (parental A673 in black bars) and in the selected CSC (in grey bars). The comparison regards AD-PC not expressing TRAIL (GFP) and AD-PC expressing TRAIL at different ratios between A673 and AD-PC (1:1; 1:2; 1:5) at 24 hours of co-culture.

DETAILED DESCRIPTION OF EMBODIMENTS OF THE INVENTION

Example 1

Isolation of pericytes from Vascular Stromal Fraction (VSF), immunophenotype characterization and gene modification: AD-PC cells were isolated from liposuctioned fat of healthy individuals through enzymatic digestion. The protocol includes processing of adipose tissue with a collagenase-based enzymatic solution. The buffer in which the lyophilized enzyme is resuspended is composed of the Low Glucose DMEM Medium (Dulbecco Modified. Eagle's Medium, Euroclone) supplemented with 1% penicilline/streptomicine (PAA, Laboratories GmbH). Adipose tissue is incubated in the enzymatic solution at 37° C. Then, 1500 rpm centrifugation is applied for 10 minutes and the cell pellet is resuspended in Low Glucose DMEM supplemented with 10% FBS (Foetal Bocine Serum, PAA, Laboratories GmbH) and 1% penicilline/streptomicine. The adipocytes left in the suspension are eliminated using a filter having 100 μm porosity (Cell Strainer, BD Falcon) and the filtrate is centrifuged at 1500 rpm for 10 minutes. The pellet so obtained is resuspended and cells are counted by 0.4% trypan blue exclusion (Cambrex) (Cell counting in a Burker chamber using a 10× reverse microscope). Cells are later plated in a standard medium (PAA, Laboratories GmbH) supplemented with 1% penicilline/streptomicine and 1% L-Glutamine (PAA, Laboratories GmbH).

Immonophenotypic analysis was carried out for cultures at step 4. After trypsinization, cells were pelleted, resuspended in 100 μl blocking buffer and incubated for 30 minutes at 4° C. Then, the sample was incubated with the antibodies of interest, diluted in 90 μl PBS and 0.5% ABS (Albumin Bovine Serum, Sigma), for 20 minutes at 4° C.

The antigens whose expression was to be assessed were: CD45, CD31, CD146, TRAIL-R1, TRAIL-R2.

The cells so labeled were analyzed by a FACScalibur cytofluorimeter (Becton-Dickinson).

The ELISA assay allowed quantification of the OPG amount released by the cells of the supernatant.

The supernatant of AD-PC and bone marrow MSC was assayed according to the protocol for the Quantikine Human OPG/TNFRSF11B kit (R&D Systems, France) used for this assay.

Creation of the retroviral vector encoding solubile TRAIL (ΔTRAIL): the election strategy that was employed for cloning the SS-FurinCV-ILC-DTRAIL molecule in a retroviral vector was as follows: The total RNA isolated from peripheral blood mononuclear cells of a healthy donor was back-transcripted by means of SuperScript™ Reverse Transcriptase (Invitrogen, USA), using 2 μg total RNA as a template and random hexamers (Roche, Germany) as primers.

The encoding fragment for the extracytoplasmatic portion of TRAIL corresponding to amino acids 114-281 was obtained by PCR, from cDNA pool, with special primers: 5'-CAGATCTGGTGAGAGAAAGAGGTCCTCAGA-GAGTA-3' (containing the cleavage site for BgIII) and 5'-GGAATTCCTTAGCCAACTAAAAAGGCCCC-3' (including the cleavage site for EcoRI). By ligase reactions, the secretion signal, the specific cleavage site of the signal sequence (Furin-CV) and the trimerization domain (ILZ) were placed at the 5' end of the gene sequence. The trimerization domain (ILZ) and the cleavage site obtained by PCR overlapping, were digested by the restriction enzymes XhoI-HindIII and HindIII-BgIII respectively. The two fragments were later cloned together with the extracytoplasmatic portion of TRAIL in a retroviral vector.

Creation of an AD-PC population stably expressing the soluble ΔTRAIL protein, and check of protein expression by Western Blot, cytofluorimetric analysis and ELISA assay: the creation of a retrovirus population capable of infecting the cell population of interest represented by AD-PC was articulated through two steps. The first step based on the obtainment of a cell line producing the retrovirus in transient mode and the second step aimed at obtaining the generation of a packaging cell line (PCL) capable of stably producing a retroviral progeny. For the transient step, embryonic renal fibroblasts (293 T cells), held at about 70% confluence were transfected with a solution of 5 μg (in a 25 cm² flask) total plasmid DNA and with the help of polycations. Later, the retroviral supernatant obtained by transient transfection of 293T was collected and used to infect the producer cell line (PLC) deriving from a human fibrosarcoma line; 24 h after infection the cells were analyzed by cytofluorimetry to check positivity of green fluorescent protein (GFP), an infection efficiency marker.

The retroviral supernatant collected by the stably ΔTRAIL-producing PCLs was collected and used to infect AD-PC cells. At least 3 infections, at 30 days from each other were performed with the same PCL, showing the stability of retroviral production.

AD-PC cells were seeded at a concentration of $5.7 \times 10^3/cm^2$ 12 hours before infection, after replacement of the medium with a medium supplemented with a retroviral supernatant and 6 μg/ml polybrene, then the cells were left for 6 hours in an incubator at 37° C., 5% CO2. The infection procedure was repeated for three days. Then, the cells were left in a standard medium for a few days before cytofluorimetric analysis to check GFP protein expression. ΔTRAIL protein production by infected AD-PC cells was assessed by Western Blot, cytofluorimetric analysis and ELISA assay.

Western Blot analysis allowed protein identification both in the cell lysate and the supernatant.

In short, the ΔTRAIL protein-expressing AD-PC cells were lysed in a lysis-buffer (50 mM Tris-HCl, pH 7.4, 150 mM NaCl, 1% NP-40, 1% Na-deoxycholate, 1 mM EDTA, 0.1% SDS, Complete protease inhibitor). Protein concentration was determined by a Bio-Rad protein assay (Bio-Rad Laboratories, Italy), cell lysates and cell supernatants were run on 8% polyacrylamide gel.

Protein detection was allowed by incubation of the nitrocellulose filter with anti-h-TRAIL (K-18) goat polyclonal antibody (Santa Cruz Biotechnology, Inc., USA) as a primary antibody and anti-goat IgG-HRP (1:10000, Santa Cruz Biotechnology, Inc., USA) as a secondary antibody.

Cytofluorimetric analysis, that allowed detection of the protein in the cytoplasm of the cell, was carried out as follows: about 7 days after infection, the cells (500,000 cells/sample) were collected and permeabilized by Perm/Wash buffer (BD Biosciences, USA) and then were incubated with the PE conjugated anti-human TRAIL CD253 antibody (BioLegend, USA) and finally analyzed by a FACSCalibur cytofluorimeter (BD Biosciences, USA). Monoclonal PE conjugated mouse IgGI, kAs antibody (BD Biosciences, USA) was used as a control isotype.

The ELISA assay allowed quantification of the ΔTRAIL amount released by the cells of the supernatant.

The supernatant of ΔTRAIL-expressing AD-PC cells and the AD-PC infected by the empty vector, was assayed according to the protocol for the Quantikine Human TRAIL/TNFSF10 kit (R&D Systems, France) used for this assay.

Results 1

Figure 1:
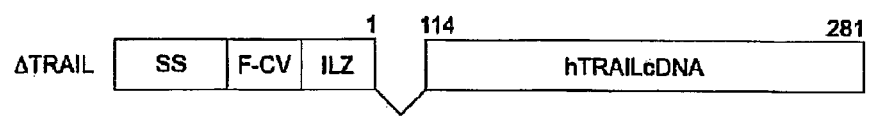

In order to develop a retroviral vector encoding a soluble TRAIL form, the encoding region for the extracytoplasmatic portion of the molecule, having a pro-apoptotic biological activity, was fused with a sequence encoding a secretion signal (derived from the immunoglobulin heavy chain) and with a trimerization domain (FIG. 1).

The soluble TRAIL solution so obtained was inserted in a retroviral vector also containing the GFP gene. A retroviral vector containing the GFP gene only was used as a control. These two vectors were used to transduce the pericytes isolated from adipose tissue in view of testing the actual anti-tumor activity of ΔTRAIL-expressing pericytes (AD-PC$^{\Delta TRAIL}$).

The success of the AD-PC infection process using a retroviral vector was assessed by reverse fluorescence microscopy (FIGS. 2A, 2B, 2C, 2D, 2E, 2F). The optimal results of the infection process is confirmed by the presence of a wholly GFP-positive, fluorescent population (FIGS. 2D and 2F), whereas the uninfected control (FIG. 2B) is negative when observed in the fluorescence channel.

The AD-PC cells isolated from the Vascular Stromal Fraction (VSF) and observed in a microscope show a fibroblast morphology (FIG. 3A), which is not subjected to changes upon genetic modification (FIGS. 3B and 3C). Then, the AD-PC cells were subjected to immunophenotypic assessment by cytofluorimetric analysis to check the expression of the typical markers of these cells before and after retroviral vector infection. It is noted that the immunophenotypic analysis of retroviral vector infected AD-PC cells (FIG. 4, lower panel at the center) is identical to that of uninfected AD-PC cells (FIG. 4, top panel), which indicates that the retroviral infection does not alter the expression of the characteristic phenotypic markers of the selected cell vector. Furthermore, the poor TRAIL-R1 and TRAIL-R2 expression, still shown by cytofluorimetric analysis, justifies the selection of AD-PC cells as cell vectors for carrying TRAIL (FIG. 5a). Such reduced expression of these receptors, when compared with that shown by TRAIL-sensitive cells, such as HeLa (cervical cancer cell line), makes the AD-PC cells insensitive to apoptotic action exerted by trail and protects them from ligand-induced death.

Finally, still with the aim of evaluating the effectiveness of the selected cell carrier, the levels of OPG released in the supernatant by AD-PC cells were assayed by ELISA.

As frequently mentioned in the art, OPG acts as a "decoy" receptor which means that, since it is a soluble molecule having a good binding affinity for TRAIL, it can bind and sequester it thereby preventing any interaction thereof with TRAIL-R1 and TRAIL-R2 receptors and hence causing its biological activity to be blocked.

Therefore, the production of large amounts of OPG by the cell carried would prevent the use of such cell carrier in a TRAIL-mediated anti-tumor strategy, because most of the TRAIL produced by the cell would be readily sequestered by the OPG in the supernatant, and the anti-tumor effect would be consequently lost.

Nevertheless, as shown in FIG. 6, the levels of OPG produced by AD-PC cells, both as a ligand soluble in the supernatant and as an intracytoplasmatic protein are irrelevant when compared with those produced by bone marrow mesenchymal stem cells MSC, that are mentioned in the art as carriers for TRAIL, which further confirms the novelty of the use of AD-PCs as a cell carrier.

The transduced AD-PC cells were assayed to check actual TRAIL expression by cytofluorimetric analysis and Western Blot.

When looking at the Western Blot image (FIG. 7) the TRAIL protein band can be identified both in the cell lysate of AD-PC$^{\Delta TRAIL}$, confirming the presence of the protein at intracytoplasmatic level, and in the supernatant, confirming that, once the protein has been produced by the cell, it is excreted into and extracytoplasmatic environment. This is particularly relevant when considering that, for the suggested application, the cell would be infused in the organism, whereby TRAIL excretion in an extracytoplasmatic environment would cause release thereof in the blood flow, thereby leading to a systemic anti-tumor effect independent of the position of the cell carrier relative to the tumor mass.

Protein production by AD-PC$^{\Delta TRAIL}$ cells was also validated by submitting the cells to cytofluorimetric analysis (FIG. 8), which allowed identification of TRAIL at intracytoplasmatic level thereby confirming Western Blot analysis.

The next step after protein identification was quantification by ELISA assay. TRAIL values released in culture media by AD-PC, AD-PC$^{GFP}$ and AD-PC$^{\Delta TRAIL}$ cells were assayed at 8, 24, 48 hours' growth. The detected values (200-400 ng/ml) are not susceptible of relevant changes at the different time intervals. This may be indicative of the fast protein turnover: the amount of degraded protein corresponds to that of produced protein (FIG. 9).

Example 2

Evaluation of the cytotossic effect of ΔTRAIL on tumor cells: HeLa tumor cells were seeded in 24 well plates at a concentration of $6×10^3$/well in triplicate 24 hours before the assay.

The supernatant, that was left in contact with AD-PC$^{\Delta TRAIL}$ or AD-PC$^{GFP}$ cells for 4, 24 and 48 hours was collected to replace the medium in the wells in which the tumor cells had been seeded. Cell viability and necrosis were assessed after 4, 24 and 48 hours by propidium iodide staining (50 µg/ml) followed by cytofluorimetric analysis. As a positive control, the same tumor cells, under the same conditions, were placed in contact with 20 ng/ml recombinant soluble human TRAIL protein (Peprotech, Rocky Hill, N.J.).

Caspase-8 activation assay: the activation of caspase-8, an enzyme involves in TRAIL-mediated early pro-apoptotic pathway is assessed as follows: HeLa tumor cells are put in contact with the supernatant collected from AD-PC$^{\Delta TRAIL}$. A negative control is also prepared, which consists of the same sample with the addition of a caspase inhibitor (Z-VAD-FMK 10 µM). After 4 and 8 hours treatment, the cells are trypsinized, resuspended in 300 µl PBS and incubated for 45 minutes at 37° in the dark with RED-IETD-FMK (sulforhodamine conjugate). The bond of this molecule to caspase-8, activated in apoptopic cells is detected by fluorescence using a cytofluorimeter.

Results 2

When looking at the reverse microscopy images that show the morphology of HeLa cells when in contact with the supernatant of AD-PC$^{\Delta TRAIL}$ cells (FIG. 11A, higher) as compared with that of HeLa in contact with the supernatant of AD-PC$^{GFP}$ cells (FIG. 11A, lower) cell distress is found in the former case, which is characterized by the presence of a large number of apoptotic bodies and debris fluctuating in the medium. The mortality of HeLa placed in contact with the supernatant of AD-PC$^{\Delta TRAIL}$ cells was quantified by cytofluorimetric analysis using propidium iodide (PI). PI is a non vital stain intercalating in the DNA of necrotic and advanced apoptotic cells.

Cytofluorimetric representation of 24 hours mortality of Hela in contact with the supernatant of AD-PC$^{\Delta TRAIL}$ cells as shown in FIG. 11B (higher) where the peak of positive PI cells is found to be displaced toward high fluorescence values as compared with the corresponding peak of HeLa treated with a supernatant of AD-PC$^{GFP}$ cells (FIG. 11B lower) and to the peak of overlay-plaqued HeLa (broken line).

A more intensive analysis confirms this data: treated HeLa cells at 4, 24 and 48 hours with the supernatant deriving from hyperconfluent AD-PC$^{\Delta TRAIL}$ (30,000 cellule/cm$^2$) exhibit a mortality of more than 80%, whereas the mortality of HeLa placed in contact with the conditioned medium of AD-PC$^{GFP}$ (30,000 cells/cm$^2$) is not more than 20% (FIG. 11), Then, considering the mortality percentages of HeLa left in contact with the supernatant of lower confluence AD-PC$^{\Delta TRAIL}$ cells (15,000 cells/cm$^2$), a mortality drop will apparently occur. This result indicates the existence of a correlation between the amount of AD-PC$^{\Delta TRAIL}$ cells and the concentration of TRAIL released in the medium, as previously shown by the ELISA assay. In order to show that the mortality detected on HeLa is really induced by the anti-tumor action mediated by ΔTRAIL excreted by infected AD-PC cells, the cleavage of caspase-8, which represents the first mediator involved in the translation of the TRAIL-mediated pro-apoptotic signal was observed in tumor cells.

Cytofluorimetric analysis showed that, after 8 hours, 40% of the tumor cells treated with the supernatant of AD-PC$^{\Delta TRAIL}$ cells showed cleavage of caspase-8, which event represents an early step in the apoptotic process of the cell, and at the same time staining with 7AAD (analog of propidium, late death stain) shows 50% of necrotic cells, these values are definitely higher than those obtained with recombinant TRAIL (20 ng) which correspond to 8 h at 25% for caspase-8 activation and 10% for 7AAD positivity (FIG. 12). Finally, concerning the controls treated with the supernatant of AD-PC$^{GFP}$ cells, caspase-8 activation and 7AAD positivity reach values comparable to the untreated control. The presence of the caspase-8 inhibitor (Z-VAD-FMK) in the TRAIL containing supernatants brings the percentage of positive cells to values comparable to the control of untreated cells or cells treated with the supernatant derived from AD-PC$^{GFP}$ cells, and a similar situation is observed 7AAD positivity is evaluated in the presence of the inhibitor, the death of cells is reduced in the presence of Z-VAD-FMK. An identical behavior, although with slightly lower percentage values, is obtained for the 4 treatment hours.

Figure 12B:
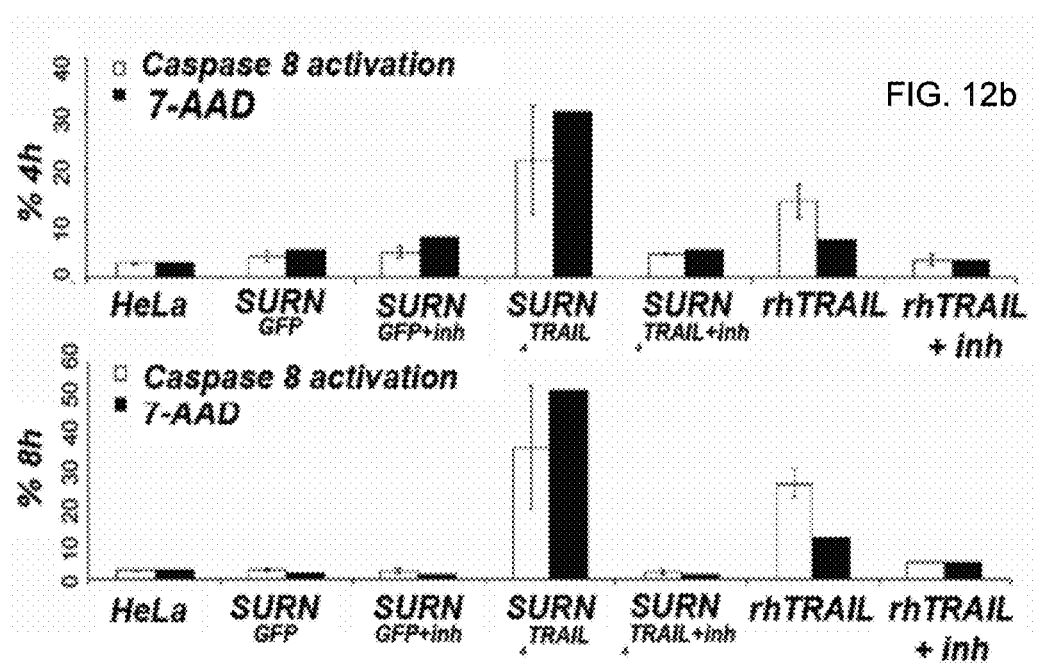

This data both confirms that the mortality encountered with treated tumor cells is really mediated by the anti-tumor action exerted by the TRAIL excreted by infected AD-PC cells, and reinforce the data obtained by analysis with PI, which showed, at 12 hours from treatment, 80% mortality correlating with 40% of early apoptosis cells (caspase-8 positive) and with 50% of late apoptosis cells (7AAD positive) encountered at 8 hours (FIG. 12B).

Example 3

Assessment of the in vivo anti-tumor effect of AD-PC$^{\Delta TRAIL}$ cells: for in vivo studies, eight-ten week NOD.CB17-Prkdc$^{scid}$/J mice were used, according to the guidelines of experimental protocols (Prot./n.543) approved by the ethic committee on animal experimentation of the University of Modena and Reggio Emilia. $2×10^5$ HeLa in 200 µl di PBS were subcutaneously administered to the animals. The tumor disappeared about two weeks later, its size being constantly monitored by means of a tumorimeter. Tumor volume was calculated using the formula: volume=length×height$^2$/2.

As the tumor appeared, the mice were divided into three groups, each consisting of three mice, the animals of the group A (control group) underwent additional handling or even weekly evaluation of tumor mass and weight growth, the animals of group B underwent three successive administration hits, by injection of $1×10^6$ AD-PC$^{GFP}$ resuspended in 200 µl PBS into the lateral tail vein, the animals of group C underwent three successive administration hits by injection of $1×10^6$ AD-PC$^{\Delta TRAIL}$ resuspended in 200 µl PBS 9 into the lateral tail vein.

At the end of the test (60 days), the animals were sacrificed and the tumor was excised.

In order to assess the presence of AD-PC$^{\Delta TRAIL}$ cells in tissues other than the tumor site, biopsies were performed on the spleen, liver, kidney, heart, muscle, lung, skin femur from which the DNA was extracted.

Research of AD-PC$^{GFP}$ and AD-AD-PC$^{\Delta TRAIL}$ cells in mouse healthy tissues: extraction of DNA from murine tissue was carried out using the Isolation kit (Gentra Systems). In order to detect the presence of GFP from isolated tissues, the extracted DNA was amplified using GFP-specific primers, 5'-GTAAACGGCCACAAGTTCAG-3' and 5'-TGTCGGCCATGATATAGACG-3' (PubMed DQ768212) (fragment 402 bp). The amplificability and integrity of the template have been checked by amplification of the GAPDH constitutive gene using specific primers 5'-GCAGTGGCAAAGTGGAGATT-3'; 5'-GCAGAAGGGGCGGAGATGAT-3', 308 BP (PubMed XM_973383).

Results 3

The animals were regularly monitored during testing to assess their physical conditions.

A weight analysis was weekly performed on mice receiving AD-PC, AD-PC$^{GFP}$ and AD-PC$^{\Delta TRAIL}$ inoculations and no considerable weight change has been noted (FIG. 13). Hepatic toxicity was found in the art in association with TRAIL administration, therefore careful monitoring was carried out on the activity of hepatic enzymes of inoculated animals, which did not show hepatic distress (FIGS. 14-15). This is very important, because the presence of ΔTRAIL expressing cells at systemic level (FIG. 10) in the animal was tested by assaying the serum of animals by ELISA to find the TRAIL protein. In animals inoculated with AD-PC $1\times10^5$, the detected TRAIL levels are lower than those inoculated with AD-PC $1\times10^6$ at sixty days treatment. This data provides an accurate indication on the permanence of AD-PC cells in the animals after several days from inoculation and also on constant TRAIL production thereby.

Systemic administration of AD-PC$^{\Delta TRAIL}$ cells after formation of the tumor mass (HeLa), allowed testing of both the migrating ability of said cells and their tumor growth inhibiting action. FIG. 16 shows the behavior of the tumor neoformation upon inoculation of AD-PC$^{GFP}$ and AD-PC$^{\Delta TRAIL}$. The control groups show an ascending behavior of the tumor mass growth from the fifteenth-twentieth day from inoculation, whereas the group of AD-PC$^{\Delta TRAIL}$ inoculated animals shows a quasi basal behavior of tumor formation, which can be identified by an inhibition of tumor growth.

Referring to FIG. 17, it will be appreciated that, in prior art, a membrane TRAIL-producing anti-tumor cell, whose nucleus contains an adenovirus that remains in episomal form (not integrated in the genome of said cells), produces two daughter cells when it is divided, one of which maintains the adenovirus that can produce membrane TRAIL, whereas the other is completely free of it; this causes a TRAIL production dilution effect at every cell division.

However, it is noted in FIG. 18 that, according to the invention, an anti-tumor cell with a retrovirus integrated in its nucleus, generating soluble TRAIL when it is divided, produces two identical daughter cells that both maintain the retrovirus integrated in their nuclei; therefore, both can produce soluble TRAIL, thereby eliminating the effect of dilution observed in prior art.

Referring to FIGS. 19-21, it can be seen that Ewing's sarcoma cell line A673 contains a fraction (18.45%±9.5%; FIG. 19) of CSC expressing CD133 antigen and characterized by higher expression of c-Myc in comparison to parental population (FIG. 20).

Referring now to FIG. 22, it can be seen that co-culture experiments between A673 and AD-PC it has been observed that AD-PC provoke a significant increase of CD133 positive population (from 17.5%±1.9 to 22.1%±2.7; p=0.05) and this effect is strictly related to the amount of AD-PC. This unexpected result suggests that AD-PC are able to influence the CSC proliferation, favouring the expansion of this usually quiescent tumor cell sub-population.

Referring to FIG. 23, it can be seen real time PCR experiments investigating unexpected burst in CSC growth order to identify the molecular mechanism driving this event. Surprisingly, we discovered that the direct cross-talk between AD-PC and A673 determine a significant increase in c-Myc expression levels in tumor cells. As previously described c-Myc is a proto-oncogene directly involved in cell proliferation and its up-regulation induced by AD-PC represent a possible explanation for the increase of CD133 number.

Referring to FIGS. 24 and 25, it can be seen cytotoxic experiments performed with AD-PC$^{\Delta TRAIL}$ and CSC A673 unexpectedly reveal a higher sensitivity to TRAIL apoptotic effect in comparison to parental A673. CSC significantly undergo to apoptosis reaching 76% of CSC death right after 8 ours of co-culture with AD-PC$^{TRAIL}$ at 1:5 ratio (FIG. 23).

The extraordinary and unforeseen responsiveness of CSC to TRAIL anti-tumor effect was also confirmed at 24 hours resulting in an even more tumor cell death than the one observed for parental tumor cells (FIG. 24 wherein 87% CSC A674 death vs 60% PARENTAL A673 death; p=0.03).

No tumor cell mortality was detected in co-culture with AD-PC$^{GFP}$ for all conditions tested (% Lysis Under Detection Limit=UDL).

The powerful antitumor effect displayed by AD-PC$^{TRAIL}$ on CSC is probably due to the synergism developed by the combination of C-myc up-regulation induced by AD-PC on CSC and TRAIL effect.

While the invention has been described in connection with the above described embodiments, it is not intended to limit the scope of the invention to the particular forms set forth, but on the contrary, it is intended to cover such alternatives, modifications, and equivalents as may be included within the scope of the invention. Further, the scope of the present invention fully encompasses other embodiments that may become apparent to those skilled in the art and the scope of the present invention is limited only by the appended claims.

The invention claimed is:

1. An anti-tumor medicament comprising an adipose-derived pericyte (AD-PC) stably transfected with a recombinant retroviral vector comprising a sequence encoding a secreted soluble TRAIL (sTRAIL), wherein the sTRAIL comprising, in the N- to C-terminal order, an immunoglobulin (Ig) heavy chain secretory sequence (SS), a furin-specific cleavage site, a trimerization domain, and an extracellular domain of a TRAIL having a proapoptotic activity.

2. A method of producing a medicament for treatment of a tumor comprising:
(a) preparing a recombinant retroviral vector comprising a sequence encoding a secreted soluble TRAIL (sTRAIL), wherein the sTRAIL comprising, in the N- to C-terminal order, an immunoglobulin (Ig) heavy chain secretory sequence (SS), a furin-specific cleavage site, a trimerization domain, and an extracellular domain of a TRAIL having a proapoptotic activity; and
(b) stably transfecting adipose-derived pericytes (AD-PC) with said recombinant retroviral vector,
wherein the transfected adipose-derived pericytes interact with cells of said tumor to increase tumor sensitivity to the secreted sTRAIL.

3. The method of claim 2, wherein the recombinant retroviral vector is produced stably by a producer cell line.

4. The method of claim 2, wherein the adipose-derived pericytes are human adipose-derived pericytes.

* * * * *